United States Patent
Minamio et al.

(10) Patent No.: US 10,913,184 B2
(45) Date of Patent: Feb. 9, 2021

(54) STATE MONITORING METHOD AND STATE MONITORING SYSTEM FOR THERMOSETTING RESIN

(71) Applicant: Panasonic Intellectual Property Management Co., Ltd., Osaka (JP)

(72) Inventors: Masanori Minamio, Osaka (JP); Yasuhiro Nakamura, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 300 days.

(21) Appl. No.: 16/029,021

(22) Filed: Jul. 6, 2018

(65) Prior Publication Data

US 2019/0016019 A1   Jan. 17, 2019

(30) Foreign Application Priority Data

Jul. 13, 2017  (JP) .................. 2017-136762
Jun. 1, 2018  (JP) .................. 2018-105739

(51) Int. Cl.
*B29C 35/02*  (2006.01)
*G01N 22/04*  (2006.01)
(Continued)

(52) U.S. Cl.
CPC ......... *B29C 35/0288* (2013.01); *G01N 22/04* (2013.01); *G01N 33/442* (2013.01); *B29K 2101/10* (2013.01); *B29K 2105/24* (2013.01)

(58) Field of Classification Search
CPC .. B29C 35/0288; G01N 22/04; G01N 33/442; B29K 2101/10; B29K 2105/24
(Continued)

(56) References Cited

U.S. PATENT DOCUMENTS

2013/0128435 A1* 5/2013 Mizuta ................. G02F 1/1339
                                                        361/679.01
2014/0275342 A1   9/2014 Guo et al.
(Continued)

FOREIGN PATENT DOCUMENTS

JP    09024518 A  *  1/1997
JP  2006179318 A  *  7/2006
(Continued)

OTHER PUBLICATIONS

Tonogai Saburo et al., "29. Hardening phenomenon in thermosetting resin molding materials", summary for a lecture at a symposium, Japan, 1964, vol. 14, pp. 173-178, Partial English Translation.
(Continued)

*Primary Examiner* — Alexander A Mercado
*Assistant Examiner* — Monica S Young
(74) *Attorney, Agent, or Firm* — Wenderoth, Lind & Ponack, L.L.P.

(57) ABSTRACT

A state monitoring method for thermosetting resin includes, in a curing treatment of thermosetting resin, detecting a moisture content of the thermosetting resin during the curing treatment; and determining a cross-linking state of the thermosetting resin during the curing treatment based on the detected moisture content. It is possible to determine the cross-linking state of the thermosetting resin by detecting the moisture content of the thermosetting resin during the curing treatment.

8 Claims, 6 Drawing Sheets

(51) Int. Cl.
    *G01N 33/44*     (2006.01)
    *B29K 105/24*     (2006.01)
    *B29K 101/10*     (2006.01)

(58) Field of Classification Search
    USPC .......................................................... 73/73
    See application file for complete search history.

(56) References Cited

U.S. PATENT DOCUMENTS

2015/0376338 A1* 12/2015 Fujiwara ............ C08G 73/0233
    428/195.1
2016/0213713 A1* 7/2016 Rizun ....................... A61J 1/05
2017/0190875 A1   7/2017 Fujiwara et al.
2017/0369751 A1* 12/2017 Nakagawa ............. G01N 19/04

FOREIGN PATENT DOCUMENTS

| | | | |
|---|---|---|---|
| JP | 2007285944 A | * | 11/2007 |
| JP | 2014-173090 | | 9/2014 |
| JP | 2016-088972 | | 5/2016 |
| JP | 2017160299 A | * | 9/2017 |
| WO | 2012/014499 | | 2/2012 |
| WO | 2014/122911 | | 8/2014 |

OTHER PUBLICATIONS

Tonogai Saburo et al., "1-9 Hardening characteristics of thermosetting resin molding materials [V]; The effects of preprocessing on the hardening characteristics of two-stage phenol resins", summary for a lecture at a symposium, 1970, vol. 20. No. 2, pp. 34-38, Partial English Translation.

\* cited by examiner

FIG. 4

| CURING CONDITION | | GLASS TRANSITION TEMPERATURE | MOISTURE CONTENT | HAST TEST 130 °C 85%RH | DISCOLORATION |
|---|---|---|---|---|---|
| TEMPERATURE (°C) | TIME (h) | (°C) | (%) | DEFECT RATE/NUMBER OF SAMPLES | ×: DISCOLORED |
| 100 | 1 | 80 | 0.23 | 3/100 | ○ |
| 100 | 3 | 83 | 0.18 | 1/100 | ○ |
| 100 | 5 | 81 | 0.07 | 1/100 | ○ |
| 125 | 1 | 92 | 0.22 | 1/100 | ○ |
| 125 | 3 | 108 | 0.06 | 0/100 | ○ |
| 125 | 5 | 114 | 0.08 | 0/100 | ○ |
| 150 | 1 | 107 | 0.18 | 0/100 | ○ |
| 150 | 3 | 125 | 0.05 | 0/100 | △ |
| 150 | 5 | 127 | 0.01 | 0/100 | × |

STATE MONITORING METHOD AND STATE MONITORING SYSTEM FOR THERMOSETTING RESIN

TECHNICAL FIELD

The technical field relates to a state monitoring method and a state monitoring system for determining a cross-linking state of thermosetting resin during a curing treatment.

BACKGROUND

In the related art, thermosetting resins have been applied to various applications as sealing resins for electronic materials and the like, as described in Japanese Patent Unexamined Publication No. 2016-88972. The thermosetting resin is generally produced by preparing a mixture of a curing agent and resin and heat-treating the mixture with a curing device to cure the mixture. In the thermosetting resin, cross-linking proceeds by an appropriate curing treatment to be a resin cured product having targeted physical properties (for example, strength and heat resistance).

A cross-linking density relating to the physical properties of the resin cured product changes depending on curing conditions (temperature profile) such as heating temperature and reaction time in the curing treatment. In a case where a temperature profile in the curing treatment is not appropriate, the cross-linking density of the resin cured product may be insufficient and mechanical properties (such as strength and elastic modulus) may decrease, in some cases. For example, in a case of an LED package (LED component), peeling occurs between a bonding wire and sealing resin due to deterioration over time, and moisture enters a gap between the bonding wire and the sealing resin.

When this LED package is mounted on printed circuit board resin, there is a possibility that a steam explosion may occur due to a reflow temperature to generate a disconnection. When a heating treatment is performed at a high temperature for a long time, the sealing resin itself may also be discolored. In a case of the LED package, light transmittance is thus impaired, thereby causing lower light emission luminance.

It is very important for obtaining the targeted physical properties of the resin cured product that an appropriate temperature profile is set in the curing treatment of the resin cured product. However, it is not easy to appropriately set the temperature profile.

In the related art, prototypes were manufactured by a curing treatment test and the obtained prototypes were subjected to a hardness measurement and an environmental test (such as a highly accelerated temperature and humidity stress test (HAST) and a temperature cycle test) to determine the temperature profile by trial and error. This procedure for determining the temperature profile was complicated, and it took a long time to determine the temperature profile. In addition, the cross-linking density of the resin cured product has a correlation with the physical properties of the resin cured product, but it was also difficult to directly measure the cross-linking density.

SUMMARY OF THE INVENTION

The present disclosure solves the disadvantages of the related art, and provides a state monitoring system and a state monitoring method for thermosetting resin, which are capable of determining a cross-linking state of thermosetting resin during a curing treatment.

According to the present disclosure, there is provided a state monitoring method for thermosetting resin, the method including: in a curing treatment of thermosetting resin, detecting a moisture content of the thermosetting resin during the curing treatment; and determining a cross-linking state of the thermosetting resin during the curing treatment based on the detected moisture content.

According to the present disclosure, there is provided a state monitoring system for thermosetting resin, the system including: a detector that detects a moisture content of thermosetting resin during a curing treatment; and a calculator that calculates a cross-linking state of the thermosetting resin during the curing treatment based on the moisture content detected by the detector.

According to the present disclosure, it is possible to determine the cross-linking state of the thermosetting resin by detecting the moisture content of the thermosetting resin during the curing treatment.

BRIEF DESCRIPTION OF THE DRAWINGS

FIG. 4 is a view showing test results of a curing treatment test;

DESCRIPTION OF EMBODIMENTS

Figure 1:
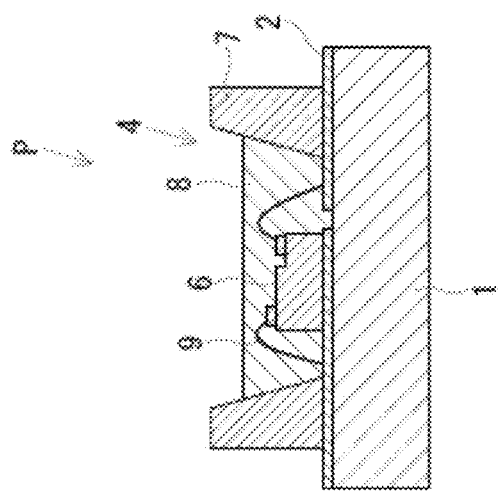
FIG. 1 is a sectional view of an LED package.

Hereinafter, curing device 100 to which a state monitoring system for thermosetting resin according to embodiments of the present disclosure is applied will be described with reference to drawings.

An example of curing device 100 is a device used in a molding step in manufacturing an LED package. Curing device 100 performs a heating treatment on thermosetting resin for sealing an LED element mounted on a board. In the drawings, the same or corresponding parts are denoted by the same reference numerals, and description thereof will not be repeated.

In the drawings to be referred to below, a configuration is simplified or schematically shown or some constituent members are omitted to make the description easier to understand. In addition, a dimensional ratio between the constituent members illustrated in each drawing does not necessarily indicate an actual dimensional ratio.

LED Package

First, LED package P which is a finished product will be described.

FIG. 1 is a sectional view of LED package P. LED package P has, for example, a function of performing irradiation with white light serving as a light source of various illumination devices. LED package P includes board 1, LED mounting portion 4, LED element 6, and sealing resin 8.

Board 1 is a portion serving as a base of LED Package P which is the finished product. In a manufacturing step, LED mounting portion 4 is formed on each of multiple boards in which a plurality of boards 1 are built. LED mounting portion 4 is a portion on which LED element 6 is mounted and liquid sealing resin 8 is applied. LED mounting portion 4 is provided with a cavity-shaped reflection portion 7 having a circular or elliptical annular bank in plan view.

LED element 6 is, for example, a blue LED, and is mounted on an inside of reflection portion 7 of each of boards 1. An electrode of LED element 6 is connected to wiring layer 2 formed on an upper surface of board 1, by bonding wire 9.

Sealing resin 8 has a function of protecting LED element 6 and bonding wire 9 and a function of transmitting the light to the outside. Therefore, sealing resin 8 is required to have high light transmittance and characteristics which hardly deteriorate due to heat or light. As sealing resin 8, for example, thermosetting resin such as epoxy resin or silicone resin is used. Sealing resin 8 is applied to an inner side of reflection portion 7 to cover LED element 6 in a liquid state, and is cured by a heating treatment for a predetermined time at a predetermined temperature by curing device 100. Sealing resin 8 contains a fluorescent substance.

In a case where LED element 6 is a blue LED, pseudo white light can be obtained by combining sealing resin 8 containing a fluorescent substance emitting fluorescent light of yellow having a complementary color relationship with blue. When sealing resin 8 is subjected to a curing treatment and then the multiple boards are cut for each board 1, LED package P is completed.

Curing Device

Curing device 100 will be described.

Figure 2:
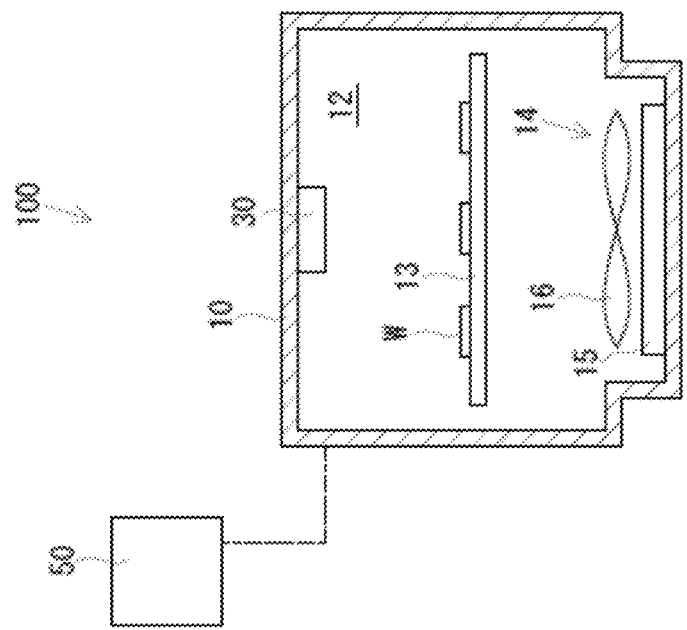
FIG. 2 is a sectional view of an outline of a curing device.

FIG. 2 is a sectional view of an outline of curing device 100. As shown in FIG. 2, curing device 100 includes heat treatment section 10, detector 30, and controller 50.

Heat treatment section 10 performs a heating treatment on the multiple boards (see FIG. 1, hereinafter referred to as workpiece W) in which liquid sealing resin 8 (thermosetting resin) is applied to LED mounting portion 4 and causes sealing resin 8 to be cured. Heat treatment section 10 has treatment space 12 and heating unit 14.

Treatment space 12 contains workpiece W. Treatment space 12 is a sealable space in which a temperature is controlled to a temperature at which sealing resin 8 is subjected to the curing treatment. In treatment space 12, heating table 13 is disposed and workpiece W is placed on heating table 13 to perform the heating treatment.

Heating unit 14 is disposed in a lower part of treatment space 12. Heating unit 14 includes heater 15, fan 16, and a temperature sensor (not shown). Heater 15 is heating means for heating treatment space 12. Fan 16 is air blowing means for circulating the heated atmosphere in treatment space 12. Heating unit 14 is controlled by controller 50 so that treatment space 12 is set to a predetermined temperature environment.

Detector 30 detects information on a state of workpiece W on which the curing treatment is performed in heat treatment section 10. Specifically, detector 30 detects a moisture content in sealing resin 8 which is applied to workpiece W. Detector 30 is a sensor that continuously detects the moisture content in the thermosetting resin during the curing treatment. As detector 30, for example, a microwave moisture sensor can be used. The microwave moisture sensor is a sensor utilizing the fact that an arrival time of a microwave is delayed according to the moisture content.

Controller 50 controls heating unit 14, thereby controlling the heating temperature and the reaction time of treatment space 12.

Controller

Figure 3:
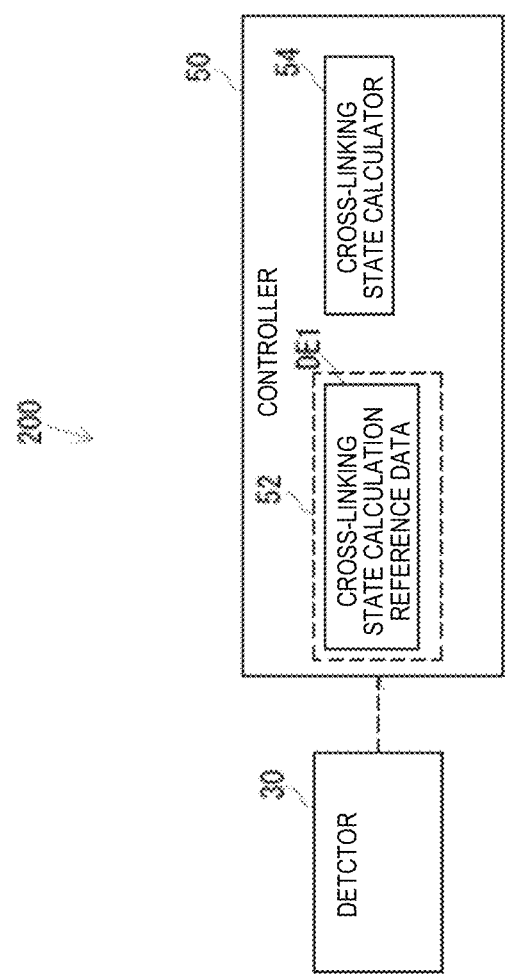
FIG. 3 is a schematic view illustrating a configuration of a curing treatment control system.

FIG. 3 is a schematic view illustrating a configuration of curing treatment control system 200.

Curing treatment control system 200 is a system that controls the curing treatment of curing device 100. In FIG. 3, in curing treatment control system 200, a configuration for determining the cross-linking state of sealing resin 8 (thermosetting resin) is mainly illustrated. Curing treatment control system 200 includes controller 50 and detector 30.

Detector 30 detects the moisture content in sealing resin 8 which is applied to workpiece W, during the curing treatment. A detection signal from detector 30 is input to controller 50. Controller 50 calculates the moisture content in sealing resin 8 based on the detection signal from detector 30.

Controller 50 includes memory 52 and cross-linking state calculator 54.

Memory 52 stores data on the cross-linking state of the thermosetting resin. Memory 52 stores cross-linking state calculation reference data DE1. In cross-linking state calculation reference data DE1, for example, the moisture content of the thermosetting resin during the curing treatment and calculation reference data on the cross-linking state of the thermosetting resin are recorded.

Although it is difficult to directly measure the cross-linking state of the thermosetting resin, according to test and study conducted by the present inventors, the following knowledge was obtained. There is a correlation between the cross-linking state and a glass transition temperature of the thermosetting resin, and there is also a correlation between the glass transition temperature and the moisture content of the thermosetting resin. From this knowledge, it is possible to derive a relationship between the moisture content of the thermosetting resin during the curing treatment and the cross-linking state of the thermosetting resin.

Cross-linking state calculator 54 calculates the cross-linking state of the sealing resin 8 during the curing treatment, based on the moisture content in sealing resin 8, the moisture content of the thermosetting resin during the curing treatment, which is stored in cross-linking state calculation reference data DE1, and calculation reference data on the cross-linking state of the thermosetting resin.

FIG. 4 shows test results of curing treatment tests respectively conducted at different heating temperature and reaction time. FIG. 4 shows test results on the relationship between curing conditions (heating temperature and reaction time), the glass transition temperature, and the moisture content, an HAST test, and presence or absence of discoloration.

As shown in FIG. 4, between the curing conditions, the glass transition temperature, and the moisture content, there is a tendency that, as the heating temperature is high and the reaction time is long, the moisture content becomes small and the glass transition temperature rises. In addition, as the glass transition temperature is relatively low and the moisture content is relatively high, there is a tendency that the defect rate in the HAST test increases. Therefore, it is presumed that, as the glass transition temperature is relatively low and the moisture content is relatively high, the cross-linking density is insufficient.

Figure 6:
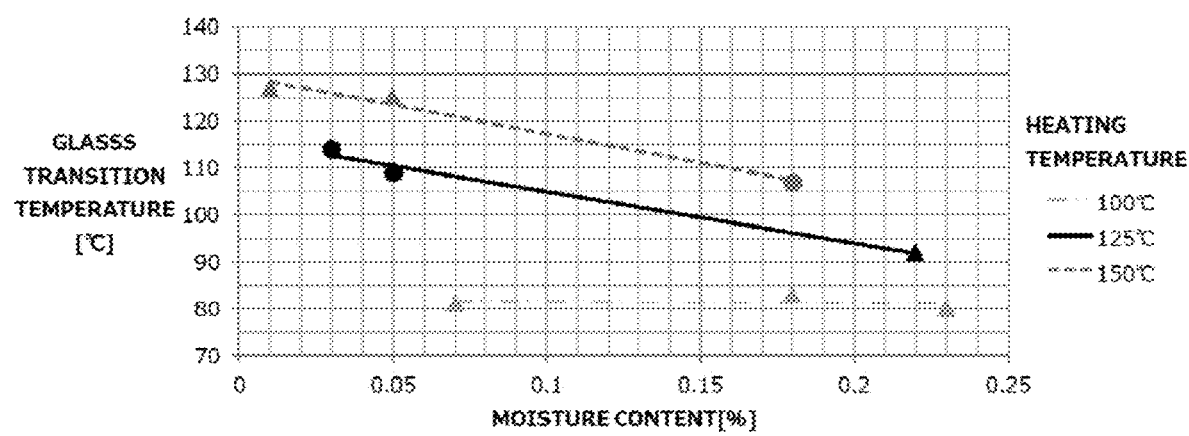
FIG. 6 is a view graphically showing the test results of FIG. 4 and illustrating an area in which cross-linking is stable.

On the other hand, it is also shown that when the glass transition temperature is relatively high and the curing time is relatively long, there is discoloration of the thermosetting resin. From this knowledge, it is possible to derive a relationship between the moisture content of the thermosetting resin during the curing treatment and the cross-linking state of the thermosetting resin, by accumulating the test results as shown in FIG. 4. FIG. 6 is a view graphically showing data shown in FIG. 4. From FIG. 6, it is found that, at the glass transition temperature of 120° C. or higher, the moisture content is 0.03% to 0.05% (125° C., 3 hours or longer) which is preferable.

The glass transition temperature of the thermosetting resin can be measured by a differential scanning calorimeter (DSC). The differential scanning calorimeter is a device that detects a change in heat flow accompanying heat absorption and heat generation to observe a curing reaction of the thermosetting resin.

Cross-Linking State Calculation Flow

Figure 5:
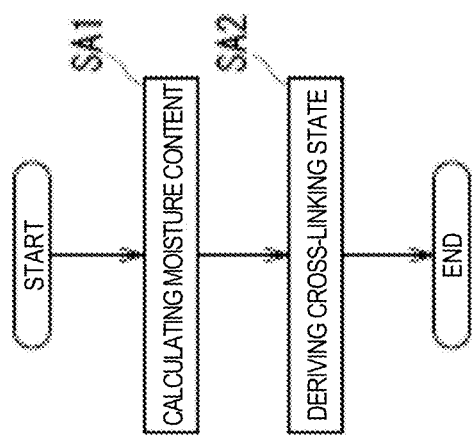
FIG. 5 is a flowchart illustrating a flow of calculating a cross-linking state of sealing resin during the curing treatment based on a moisture content.

FIG. 5 is a flowchart illustrating a flow of calculating the cross-linking state of sealing resin 8 during the curing treatment based on the moisture content in sealing resin 8.

When a cross-linking state calculation flow shown in FIG. 5 starts, first, controller 50 calculates the moisture content in sealing resin 8 based on the detection signal from detector 30 in Step SA1.

In Step SA2, cross-linking state calculator 54 refers to cross-linking state calculation reference data DE1 stored in memory 52, and calculates the cross-linking state of sealing resin 8 during the curing treatment based on the moisture content in sealing resin 8 to finish the flow.

According to curing device 100 described above, it is possible to determine the cross-linking state of the thermosetting resin by detecting the moisture content of the thermosetting resin during the curing treatment. In addition, it is possible to determine the cross-linking state of the thermosetting resin during the curing treatment, by a step of detecting the moisture content of the thermosetting resin during the curing treatment and a step of calculating the cross-linking state of the thermosetting resin based on the detected moisture content.

It is possible to determine the cross-linking state of the thermosetting resin during the curing treatment, by detecting the moisture content of the thermosetting resin during the curing treatment by detector 30 and calculating the cross-linking state of the thermosetting resin by cross-linking state calculator 54 based on the detected moisture content.

It is possible to determine the cross-linking state of the thermosetting resin during the curing treatment by calculating the cross-linking state of the thermosetting resin based on the relationship stored in memory 52 between the moisture content of the thermosetting resin and the cross-linking state of the thermosetting resin.

Modification Example

The state monitoring method and the state monitoring system for thermosetting resin according to the present disclosure are not limited to the above-described embodiment. In addition, a curing device to which the present disclosure is applied is also not limited to the embodiment.

For example, the curing device of the embodiment calculates the cross-linking state of sealing resin 8 during the curing treatment based on the moisture content in sealing resin 8. However, the curing conditions (temperature profile) such as the heating temperature and the reaction time in the curing treatment may be controlled based on the calculated cross-linking state.

Specifically, controller 50 determines the cross-linking state of sealing resin 8 during the curing treatment based on the moisture content detected by detector 30 and contained in sealing resin 8, and controls heating unit 14 based on the cross-linking state of sealing resin 8. Accordingly, controller 50 performs the heating treatment at an appropriate temperature profile on workpiece W.

In this case, for example, even in a case of various different types of LED packages or LED packages on which the heating treatment is performed for the first time, it is possible to control the temperature profile during the heating treatment and appropriately perform the curing treatment from the beginning, without determining the curing conditions in advance.

In addition, in the embodiment, a batch type curing device has been described, but a continuous type curing device which performs heating while being conveyed may be adopted. In a case of the continuous type curing device, for example, it is possible to perform the heating treatment at an appropriate temperature profile for workpiece W by controlling a conveying speed based on the state of sealing resin 8 of workpiece W.

In the embodiment, the cross-linking state was determined by deriving the glass transition temperature from the moisture content in sealing resin 8, but is not limited to only using the glass transition temperature. For example, the cross-linking state may be determined by deriving hardness from the moisture content in sealing resin 8.

As above, although the embodiment of the present disclosure was described, the above-described embodiment is merely an example for implementing the present disclosure. Accordingly, the present disclosure is not limited to the above-described embodiment, and the above-described embodiment can be appropriately modified and implemented without departing from the spirit of the present disclosure.

The state monitoring method and the state monitoring system for thermosetting resin according to the present disclosure can be used for a curing treatment for thermosetting resin.

The controller 50 can be a processor configured according to instructions stored in a memory (not shown) to calculate the cross-linking state of the thermosetting resin during the curing treatment based on the moisture content detected by the detector. That is, the cross-linking state calculator 53 may be implemented by the controller 50 executing the instructions or logic.

What is claimed is:

1. A method for monitoring a state change of thermosetting resin from liquid to solid, the method comprising; during a curing treatment of thermosetting resin-detecting a moisture content of the thermosetting resin during the curing treatment using a heating unit in a heat treatment section of a curing device; calculating a glass transition temperature of the thermosetting resin based on the detected moisture content by an electro-magnetic wave based moisture detector; and determining a cross-linking state of the thermosetting resin during the curing treatment based on the calculated glass transition temperature, wherein the glass transition temperature is in a range of 107° C. to 114° C., inclusive; and wherein the heating unit in the heat treatment section is controlled based on the calculated cross-linking state.

2. A method for monitoring a state change of thermosetting resin from liquid to solid, the method comprising; during a curing treatment of thermosetting resin a step of detecting a moisture content of the thermosetting resin during the curing treatment using a heating unit in a heat treatment section of a curing device; a step of calculating a glass transition temperature of the thermosetting resin based on the detected moisture content by an electro-magnetic wave based moisture detector; and a step of calculating a cross-linking state of the thermosetting resin during the curing treatment based on the calculated glass transition temperature, wherein the glass transition temperature is in a range of 107° C. to 114° C., inclusive; and wherein the heating unit in the heat treatment section is controlled based on the calculated cross-linking state.

3. The method for monitoring a state change of thermosetting resin from liquid to solid according to claim 2,
wherein the moisture content of the thermosetting resin is 0.03% to 0.05%.

4. A system for monitoring a state change of thermosetting resin from liquid to solid, the system comprising: an electromagnetic wave based detector configured to detect a moisture content of thermosetting resin during a curing treatment including a heating unit in a heat treatment section of a curing device; and a calculator configured to calculate (1) a glass transition temperature of the thermosetting resin during the curing treatment based on the detected moisture content detected by the electromagnetic wave based detector, and (2) a cross-linking state of the thermosetting resin during the curing treatment based on the calculated glass transition temperature, wherein the glass transition temperature is in a range of 107° C. to 114° C., inclusive; and wherein the heating unit in the heat treatment section is controlled based on the calculated cross-linking state.

5. The system for monitoring a state change of thermosetting resin from liquid to solid according to claim 4, the system further comprising:
a non-transitory storage unit configured to store a relationship between the moisture content of the thermosetting resin and the cross-linking state of the thermosetting resin,
wherein the calculator is configured to calculate the cross-linking state of the thermosetting resin during the curing treatment, based on the moisture content detected by the detector and the relationship stored in the non-transitory storage unit between the moisture content of the thermosetting resin and the cross-linking state of the thermosetting resin.

6. The system for monitoring a state change of thermosetting resin from liquid to solid according to claim 5,
wherein the moisture content of the thermosetting resin is 0.03% to 0.05%.

7. The system for monitoring a state change of thermosetting resin from liquid to solid according to claim 4,
wherein the detector is a microwave moisture sensor.

8. The system for monitoring a state change of thermosetting resin from liquid to solid according to claim 4, wherein the calculator is a controller, the controller including instructions stored in a non-transitory memory, the instructions for configuring the controller to calculate (1) the glass transition temperature of the thermosetting resin during the curing treatment based on the detected moisture content detected by the detector, and (2) the cross-linking state of the thermosetting resin during the curing treatment based on the calculated glass transition temperature.

* * * * *